(12) United States Patent
Salce, Jr. et al.

(10) Patent No.: US 9,956,158 B2
(45) Date of Patent: May 1, 2018

(54) TOPICAL HAIR GROWTH FORMULATION

(71) Applicant: SYNERGISTIC THERAPEUTICS, LLC, Naples, FL (US)

(72) Inventors: Anthony H. Salce, Jr., Naples, FL (US); William F. Greenwood, Fairfield, CT (US); Shivsankar Misir, Naples, FL (US)

(73) Assignee: Synergistic Therapeutics, LLC, Naples, FL (US)

( * ) Notice: Subject to any disclaimer, the term of this patent is extended or adjusted under 35 U.S.C. 154(b) by 0 days. days.

(21) Appl. No.: 15/699,414

(22) Filed: Sep. 8, 2017

(65) Prior Publication Data

US 2018/0064621 A1 Mar. 8, 2018

Related U.S. Application Data

(60) Provisional application No. 62/384,984, filed on Sep. 8, 2016.

(51) Int. Cl.

| | |
|---|---|
| *A61K 31/195* | (2006.01) |
| *A61K 31/135* | (2006.01) |
| *A61K 31/44* | (2006.01) |
| *A61K 31/58* | (2006.01) |
| *A61K 31/505* | (2006.01) |
| *A61K 31/56* | (2006.01) |
| *A61K 31/519* | (2006.01) |
| *A61K 8/63* | (2006.01) |
| *A61K 8/44* | (2006.01) |
| *A61K 8/41* | (2006.01) |
| *A61K 8/49* | (2006.01) |
| *A61Q 7/00* | (2006.01) |

(52) U.S. Cl.
CPC .................. *A61K 8/63* (2013.01); *A61K 8/41* (2013.01); *A61K 8/44* (2013.01); *A61K 8/4926* (2013.01); *A61K 8/4953* (2013.01); *A61Q 7/00* (2013.01)

(58) Field of Classification Search
USPC .... 514/171, 177, 265.1, 275, 284, 291, 561, 514/649
See application file for complete search history.

(56) References Cited

U.S. PATENT DOCUMENTS

| | | | | |
|---|---|---|---|---|
| 4,912,111 | A * | 3/1990 | Sank | A61K 31/505 514/256 |
| 6,576,259 | B2 * | 6/2003 | Yamashita | A61K 9/141 424/400 |
| 6,849,661 | B2 * | 2/2005 | Kelly | A61K 31/277 514/523 |
| 6,936,599 | B2 * | 8/2005 | Voskuhl | A61K 31/56 514/16.6 |
| 7,799,331 | B2 * | 9/2010 | Asotra | A61K 9/0095 424/400 |
| 7,998,970 | B2 * | 8/2011 | Soskic | A61K 31/568 435/189 |
| 9,260,438 | B2 * | 2/2016 | Bodhuri | C07D 487/04 |
| 9,539,332 | B2 * | 1/2017 | Pacetti | A61L 27/34 |

* cited by examiner

*Primary Examiner* — Raymond J Henley, III
(74) *Attorney, Agent, or Firm* — Moritt Hook & Hamroff LLP; Steven S. Rubin, Esq.

(57) ABSTRACT

Technologies are described for a formulation and production of a formulation. The methods may comprise depositing a non-steroidal anti-inflammatory drug (NSAID) compound, a calcium channel blocker, an immunosuppressive component, an anti-hypertensive, a hormone, a steroid, and an enzyme inhibitor into a chamber. The methods may comprise milling and mixing the NSAID compound, the calcium channel blocker, the immunosuppressive component, the anti-hypertensive, the hormone, the steroid, and the enzyme inhibitor into a powder. The methods may comprise adding a solvent with the powder. The methods may comprise mixing the solvent with the powder to form the formulation.

20 Claims, 2 Drawing Sheets

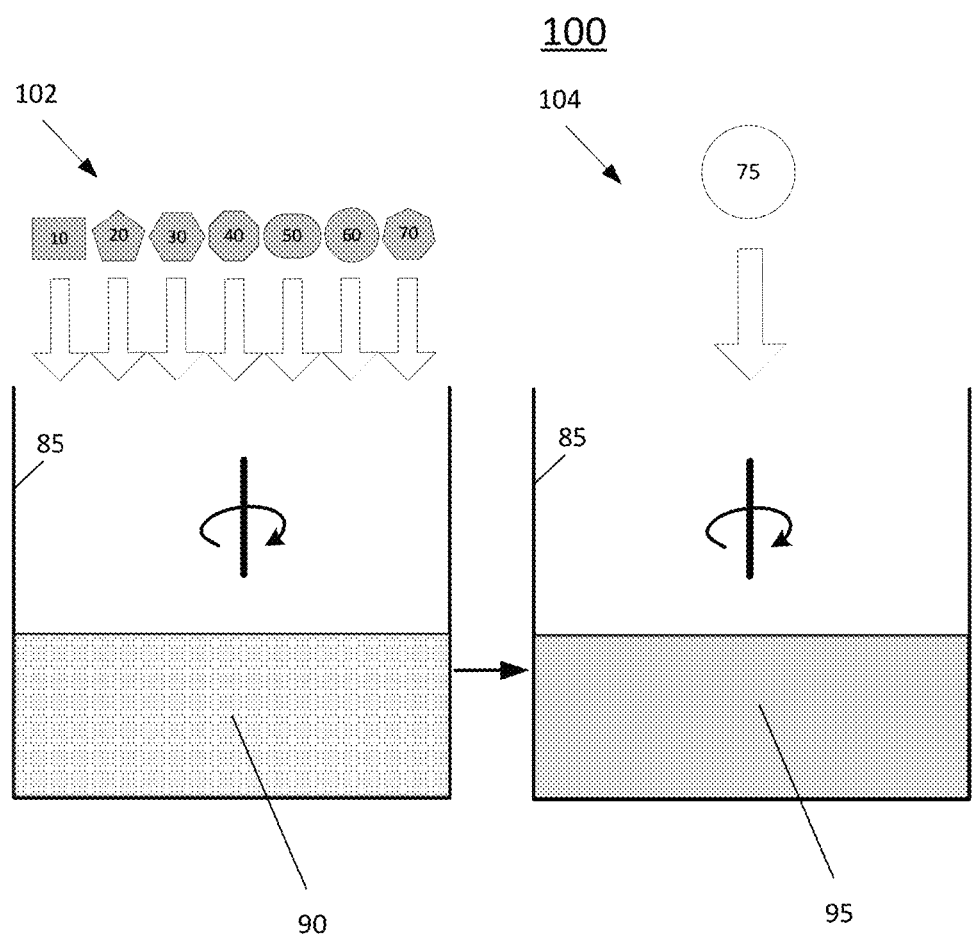

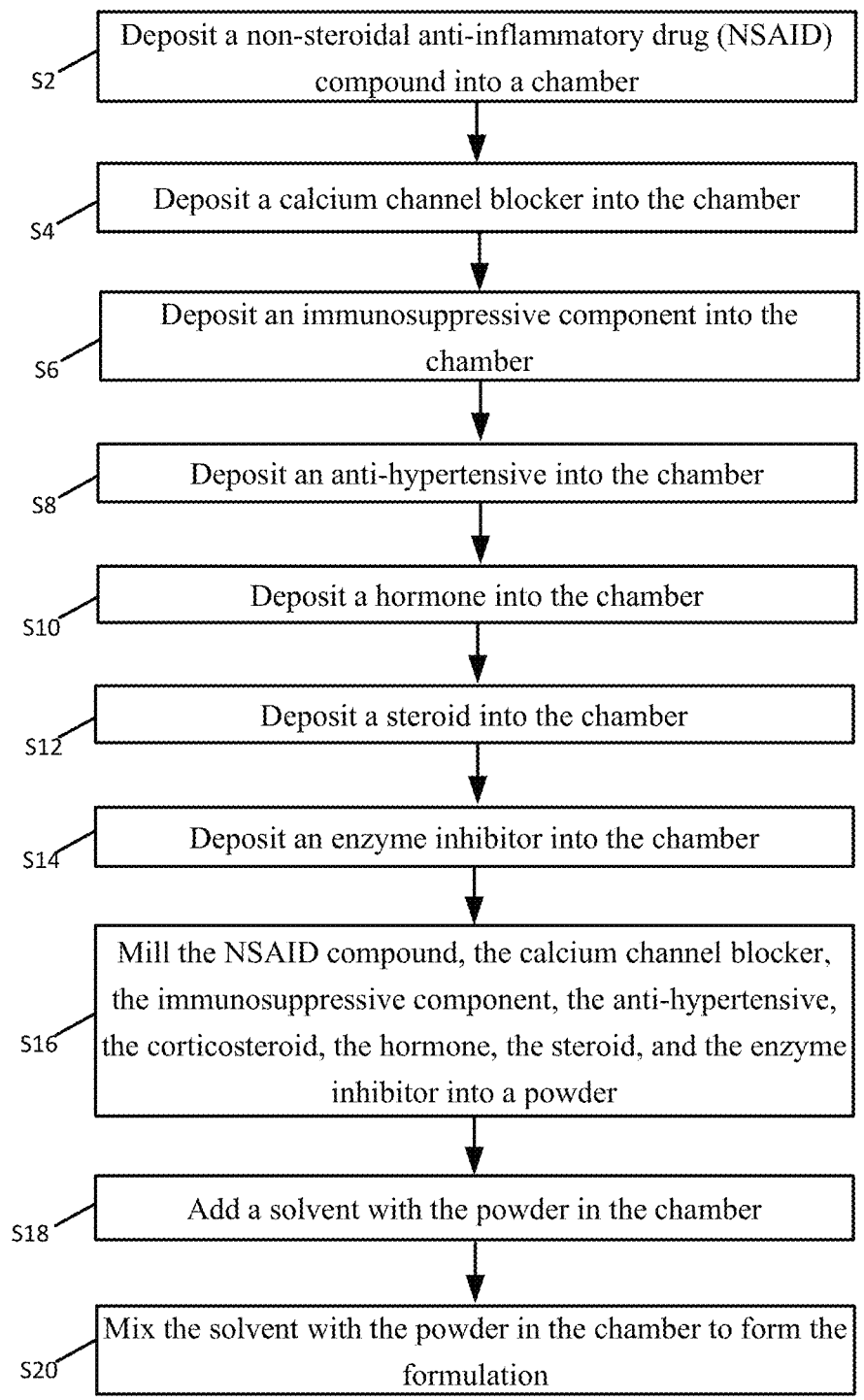

TOPICAL HAIR GROWTH FORMULATION

BACKGROUND

Androgenetic alopecia (AGA), described as hair loss and balding, is the most common type of hair loss. AGA may be caused by an androgen-dependent process which causes miniaturization of hair follicles in the scalp. Scalp dihydrotestosterone (DHT) may be a hair loss promoter formed from testosterone. Men with AGA may exhibit lower levels of total testosterone, higher levels of unbound/free testosterone, and higher levels of total free androgens including DHT. Increased DHT levels may contribute to hair loss. Hair loss in men may be genetically predisposed and may cause a disturbance in the normal hair growth cycle, leading to thinning of the hair on the head and possible balding. Hair loss in women may be due to hormonal imbalances, anemia, menopause, a protein deficiency, or a chronic medical condition.

SUMMARY

In some examples formulations are described. The formulations may comprise a non-steroidal anti-inflammatory drug (NSAID). The formulations may comprise a calcium channel blocker. The formulations may comprise an immunosuppressive component. The formulations may comprise an anti-hypertensive. The formulations may comprise a hormone. The formulations may comprise a steroid. The formulations may comprise an enzyme inhibitor.

In some examples, methods to produce a formulation are described. The methods may comprise receiving a non-steroidal anti-inflammatory drug (NSAID) compound into a chamber. The methods may comprise receiving a calcium channel blocker into the chamber. The methods may comprise receiving a calcium channel blocker into the chamber. The methods may comprise receiving an immunosuppressive component into the chamber. The methods may comprise receiving an anti-hypertensive into the chamber. The methods may comprise receiving a hormone into the chamber. The methods may comprise receiving steroid into the chamber. The methods may comprise receiving an enzyme inhibitor into the chamber. The methods may comprise milling the NSAID compound, the calcium channel blocker, the immunosuppressive component, the anti-hypertensive, the hormone, the steroid, and the enzyme inhibitor into a powder.

In some examples, formulations may be described. The formulations may comprise 2.0 to 10.0 weight percent of a non-steroidal anti-inflammatory drug (NSAID). The formulations may comprise 0.01 to 0.05 weight percent of a calcium channel blocker. The formulations may comprise 0.5 to 1.0 weight percent of an immunosuppressive component. The formulations may comprise 3.0 to 7.0 weight percent of an anti-hypertensive. The formulations may comprise 0.005 to 0.010 weight percent of a hormone. The formulations may comprise 0.1 to 0.2 weight percent of a steroid.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1 illustrates an example system that can be utilized to produce a topical hair growth formulation; and FIG. 2 illustrates a flow diagram of an example process to produce topical hair growth formulation;

all arranged according to at least some embodiments described herein.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system that can be utilized to produce a topical hair growth formulation, arranged in accordance with at least some embodiments presented herein. As discussed in more detail below, a topical hair growth formulation may be effective in the treatment of androgenetic alopecia (AGA).

System 100 may include a compound 10, a compound 20, a compound 30, a compound 40, a compound 50, a compound 60, a compound 70, a solvent 75, and a chamber 85. Compound 10 may be a non-steroidal anti-inflammatory drug (NSAID). Compound 10 may reduce substances in the body that cause pain and inflammation. Compound 10 may include diclofenac with formula $C_{14}H_{11}Cl_2NO_2$ or a diclofenac diethylammonium salt with formula $C_{18}H_{22}Cl_2N_2O_2$. Compound 10 may be deposited into chamber 85.

Compound 20 may be a calcium channel blocker. Compound 20 may be a phenylalkylamine calcium channel blocker and may treat hypertension. Compound 20 may be an ionic calcium influx inhibitor more commonly known as a calcium channel blocking agent. Compound 20 may inhibit the transmembrane influx of extracellular calcium ions across the membrane of muscle cells. Compound 20 may be verapamil with formula $C_{27}H_{38}N_2O_4$. Compound 20, by inhibiting calcium influx, may inhibit the contractile processes, and may thereby dilate the main outer layers of the skin to allow penetration of the topical lotion. Compound 20 may increase scalp permeability and may inhibit transmembrane influx of extracellular calcium ions across the membrane of vascular smooth cells. Compound 20 may increase blood flow to hair follicles by acting as a vasodilator. Compound 20 may be deposited into chamber 85.

Compound 30 may be an immunosuppressive component. Compound 30 may reduce the autoimmune reactions against hair follicle autoantigens. Compound 30 may inhibit the production of interleukin-2 in the immune system. Compound 30 may inhibit development and proliferation of nuclear factor of activated T-cells (NFAT). Compound 30 may be tacrolimus with formula $C_{44}H_{69}NO_{12}$. Compound 30 may be deposited into chamber 85.

Compound 40 may be an anti-hypertensive. Compound 40 may be a vasodilator and may widen blood vessels. Compound 40 may reduce hair loss and promote hair growth in patients with AGA. Compound 40 may be minoxidil (6-amino-1,2,-dihydro, I-hydroxy-2-imino-4-piperidinopyrimidine) with formula $C_9H_{15}N_5O$. Compound 40 may be deposited into chamber 85.

Compound 50 may be a hormone. Compound 50 may be a natural lower-potency hormone. Compound 50 may be a signaling molecule to target an organ to regulate physiology and behavior of an organism. Compound 50 may be a naturally occurring agent or a synthetic agent, and may be two or more agents combined. Compound 50 may improve or alleviate undesirable conditions of the scalp. Compound 50 may be a form of estrogen. Compound 50 may block testosterone to lower dihydrotestosterone (DHT) levels. Compound 50 may suppress the androgenetic effect of testosterone. Compound 50 be estriol with formula $C_{18}H_{24}O_3$. Compound 50 may be deposited into chamber 85.

Compound 60 may be a steroid. Compound 60 may be a synthetic androstane steroid and a 4-azasteriod. Compound 60 may be lipophilic. Compound 60 may comprise a type II and type III 5α-reductase inhibitor. Compound 60 may impede the conversion of testosterone to dihydrotestosterone (DHT). Compound 60 may be finasteride with formula $C_{23}H_{36}N_2O_2$. Compound 60 may be deposited into chamber 85.

Compound 70 may be an enzyme inhibitor. Compound 70 may inhibit the enzyme janus kinase 1 (JAK1) and janus kinase 3 (JAK3). Compound 70 may inhibit the production of inflammatory mediators and suppress signal transducer and activator of transcription 1 (STAT1) dependent genes in joint tissue. Compound 70 may be tofacitinib with formula $C_{16}H_{20}N_6O$. Compound 70 may be deposited into chamber 85.

At 102, compound 10, compound 20, compound 30, compound 40, compound 50, compound 60, and compound 70 may be deposited into chamber 85. Compound 10, compound 20, compound 30, compound 40, compound 50, compound 60, and compound 70 may be milled and mixed into a fine powder 90. Milling and mixing may be performed either by hand or machine. Powder 90 may include particulates with a particle size from 1 micron to 40 microns.

At 104, a solvent 75 may be added with powder 90 in chamber 85. Solvent 75 may be mixed with powder 90 in chamber 85 until topical hair growth formulation 95 is formed. Topical hair growth formulation 95 may include powder 90 dispersed in solvent 75. Mixing may be performed either by hand or machine. Solvent 75 may include propylene glycol, water, alcohol, or mineral oil and combinations thereof.

Compound 10 may comprise from 2.0% by weight to 10.0% by weight of topical hair growth formulation 95. Compound 20 may comprise from 0.01% by weight to 0.05% by weight of topical hair growth formulation 95. Compound 30 may comprise from 0.5% by weight to 1.0% by weight of topical hair growth formulation 95. Compound 40 may comprise from 3.0% by weight to 7.0% by weight of topical hair growth formulation 95. Compound 50 may comprise from 0.005% by weight to 0.010% by weight of topical hair growth formulation 95. Compound 60 may comprise from 0.1% by weight to 0.2% by weight of topical hair growth formulation 95. Compound 70 may comprise from 1.0% by weight to 5.0% by weight of topical hair growth formulation 95.

FIG. 2 illustrates a flow diagram of an example process to produce a topical hair growth formulation 95. The process in FIG. 2 could be implemented using, for example, system 100 discussed above. An example process may include one or more operations, actions, or functions as illustrated by one or more of blocks S2, S4, S6, S8, S10, S12, S14, S16, S18, and/or S20. Although illustrated as discrete blocks, various blocks may be divided into additional blocks, combined into fewer blocks, or eliminated, depending on the desired implementation.

Processing may begin at block S2, "Deposit a non-steroidal anti-inflammatory drug (NSAID) compound into a chamber." At block S2, a NSAID compound may be deposited into a chamber. The NSAID compound may reduce substances in the body that cause pain and inflammation. The NSAID compound may include diclofenac with formula $C_{14}H_{11}Cl_2NO_2$ or a diclofenac diethylammonium salt with formula $C_{18}H_{22}Cl_2N_2O_2$.

Processing may continue from block S2 to block S4, "Deposit a calcium channel blocker into the chamber." At block S4, a calcium channel blocker may be deposited into the chamber. The calcium channel blocker may be a phenylalkylamine calcium channel blocker and may treat hypertension. The calcium channel blocker may be an ionic calcium influx inhibitor more commonly known as a calcium channel blocking agent. The calcium channel blocker may inhibit the transmembrane influx of extracellular calcium ions across the membrane of muscle cells. The calcium channel blocker, by inhibiting calcium influx, may inhibit the contractile processes, and may thereby dilate the main outer layers of the skin to allow penetration of the topical lotion. The calcium channel blocker may increase scalp permeability and may inhibit transmembrane influx of extracellular calcium ions across the membrane of vascular smooth cells. The calcium channel blocker may increase blood flow to hair follicles by acting as a vasodilator. The calcium channel blocker may be verapamil with formula $C_{27}H_{38}N_2O_4$.

Processing may continue from block S4 to block S6, "Deposit an immunosuppressive component into the chamber." At block S6, an immunosuppressive component may be deposited into the chamber. The immunosuppressive component may reduce the autoimmune reactions against hair follicle autoantigens. The immunosuppressive component may inhibit the production of interleukin-2 in the immune system. The immunosuppressive component may inhibit development and proliferation of nuclear factor of activated T-cells (NFAT). The immunosuppressive component may be tacrolimus with formula $C_{44}H_{69}NO_{12}$.

Processing may continue from block S6 to block S8, "Deposit an anti-hypertensive into the chamber." At block S8, an anti-hypertensive may be deposited into the chamber. The anti-hypertensive may be a vasodilator and may widen blood vessels. The anti-hypertensive may reduce hair loss and promote hair growth in patients with AGA. The anti-hypertensive may be minoxidil (6-amino-1,2,-dihydro, I-hydroxy-2-imino-4-piperidinopyrimidine) with formula $C_9H_{15}N_5O$.

Processing may continue from block S8 to block S10, "Deposit a hormone into the chamber." At block S10, a hormone may be deposited into the chamber. The hormone may be a natural lower-potency hormone. The hormone may be a naturally occurring agent or a synthetic agent, and may be two or more agents combined. The hormone may improve or alleviate undesirable conditions of the scalp. The hormone may be a form of estrogen. The hormone may block testosterone to lower dihydrotestosterone (DHT) levels. The hormone may suppress the androgenetic effect of testosterone. The hormone may be estriol with formula $C_{18}H_{24}O_3$.

Processing may continue from block S10 to block S12, "Deposit a steroid into the chamber." At block S12, a steroid may be deposited into the chamber. The steroid may be a synthetic androstane steroid and a 4-azasteriod. The steroid may be lipophilic. The steroid may comprise a type II and type III 5α-reductase inhibitor. The steroid may impede the conversion of testosterone to dihydrotestosterone (DHT). The steroid may be finasteride with formula $C_{23}H_{36}N_2O_2$.

Processing may continue from block S12 to block S14, "Deposit an enzyme inhibitor into the chamber." At block S14, an enzyme inhibitor may be deposited into the chamber. The enzyme inhibitor may inhibit the production of inflammatory mediators and suppress signal transducer and activator of transcription 1 (STAT1) dependent genes in joint tissue. The enzyme inhibitor may be tofacitinib with formula $C_{16}H_{20}N_6O$.

Processing may continue from block S14 to block S16, "Mill the NSAID compound, the calcium channel blocker, the immunosuppressive component, the anti-hypertensive, the corticosteroid, the hormone, the steroid, and the enzyme inhibitor into a powder." At block S16, the NSAID component, the calcium channel blocker, the immunosuppressive component, the anti-hypertensive, the hormone, the steroid, and the enzyme inhibitor be milled into a fine powder. The milling may be performed either by hand or machine. The powder may include particulates with a particle size from 1 micron to 40 microns.

Processing may continue from block S16 to block S18, "Add a solvent with the powder in the chamber." At block S18, a solvent may be added to the powder in the chamber. The solvent may include propylene glycol, water, alcohol, or mineral oil and combinations thereof.

Processing may continue from block S18 to block S20, "Mix the solvent with the powder in the chamber to form the formulation." At block S22, the solvent may be mixed with the powder in the chamber. The solvent may be mixed with the powder in the chamber until a clear solution is formed with the powder dispersed in the solvent to form the formulation. Mixing may be performed either by hand or machine.

A system in accordance with the present disclosure may be effective to form a topical pharmaceutical formulation that promotes hair growth and slows hair loss. An embodiment of the present application may result in a formulation that suppresses inflammation and increases blood flow in areas where it is applied. An embodiment of the present application may result in a formulation that provides high scalp penetration with complete dissolution of the emulsion and little to no irritation. An embodiment of the present application may result in a formulation that has high stability and provides a significantly higher percentage of patients with hair growth and slowing of hair loss than previous formulations.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A formulation comprising:
   a non-steroidal anti-inflammatory drug (NSAID);
   a calcium channel blocker;
   an immunosuppressive component;
   an anti-hypertensive;
   a hormone;
   a steroid; and
   an enzyme inhibitor.

2. The formulation of claim 1, further comprising:
   2.0 to 10.0 weight percent of the non-steroidal anti-inflammatory drug (NSAID);
   0.01 to 0.05 weight percent of the calcium channel blocker;
   0.5 to 1.0 weight percent of the immunosuppressive component;
   3.0 to 7.0 weight percent of the anti-hypertensive;
   0.005 to 0.010 weight percent of the hormone;
   0.1 to 0.2 weight percent of a steroid; and
   1.0 to 5.0 weight percent of the enzyme inhibitor.

3. The formulation of claim 1, wherein the NSAID includes diclofenac and has a formula of $C_{14}H_{11}Cl_2NO_2$ or a diclofenac diethylammonium salt with a formula of $C_{18}H_{22}Cl_2N_2O_2$.

4. The formulation of claim 1, wherein the calcium channel blocker includes verapamil with a formula of $C_{27}H_{38}N_2O_4$.

5. The formulation of claim 1, wherein the immunosuppressive component includes tacrolimus with a formula of $C_{44}H_{69}NO_{12}$.

6. The formulation of claim 1, wherein the anti-hypertensive includes minoxidil (6-amino-1,2,-dihydro, I-hydroxy-2-imino-4-piperidinopyrimidine) with formula $C_9H_{15}N_5O$.

7. The formulation of claim 1, wherein the hormone includes estriol with formula $C_{18}H_{24}O_3$.

8. The formulation of claim 1, wherein the steroid includes finasteride with formula $C_{23}H_{36}N_2O_2$.

9. The formulation of claim 1, wherein the enzyme inhibitor includes tofacitinib with formula $C_{16}H_{20}N_6O$.

10. The formulation of claim 1, wherein:
    the NSAID includes diclofenac;
    the calcium channel blocker includes verapamil;
    the immunosuppressive component includes tacrolimus;
    the anti-hypertensive includes minoxidil;
    the first steroid includes prednisolone;
    the hormone includes estriol;
    the second steroid includes finasteride; and
    the enzyme inhibitor includes tofacitinib.

11. The formulation of claim 10, further comprising a solvent.

12. The formulation of claim 11, wherein the solvent includes propylene glycol, water, alcohol, or mineral oil and combinations thereof.

13. A method to produce a formulation, the method comprising:
    receiving a non-steroidal anti-inflammatory drug (NSAID) compound into a chamber;
    receiving a calcium channel blocker into the chamber;
    receiving a calcium channel blocker into the chamber;
    receiving an immunosuppressive component into the chamber;
    receiving an anti-hypertensive into the chamber;
    receiving a hormone into the chamber;

receiving steroid into the chamber;
receiving an enzyme inhibitor into the chamber;
milling the NSAID compound, the calcium channel blocker, the immunosuppressive component, the anti-hypertensive, the hormone, the steroid, and the enzyme inhibitor into a powder.

14. The method of claim 13, further comprising:
adding a solvent with the powder in the chamber;
mixing the solvent with the powder in the chamber to form the formulation.

15. The method of claim 13, wherein:
the NSAID includes diclofenac;
the calcium channel blocker includes verapamil;
the immunosuppressive component includes tacrolimus;
the anti-hypertensive includes minoxidil;
the hormone includes estriol;
the steroid includes finasteride; and
the enzyme inhibitor includes tofacitinib.

16. The method of claim 14, wherein the solvent includes propylene glycol, water, alcohol, or mineral oil and combinations thereof.

17. The method of claim 15, wherein the formulation includes:
2.0 to 10.0 weight percent of diclofenac;
0.01 to 0.05 weight percent of verapamil;
0.5 to 1.0 weight percent of tacrolimus;
3.0 to 7.0 weight percent of minoxidil;
0.005 to 0.010 weight percent of estriol;
0.1 to 0.2 weight percent of finasteride; and
1.0 to 5.0 weight percent of tofacitinib.

18. A formulation comprising:
2.0 to 10.0 weight percent of a non-steroidal anti-inflammatory drug (NSAID);
0.01 to 0.05 weight percent of a calcium channel blocker;
0.5 to 1.0 weight percent of an immunosuppressive component;
3.0 to 7.0 weight percent of an anti-hypertensive;
0.005 to 0.010 weight percent of a hormone; and
0.1 to 0.2 weight percent of a steroid.

19. The formulation of claim 18, further comprising:
1.0 to 5.0 weight percent of an enzyme inhibitor; and
a solvent.

20. The formulation of claim 19, wherein:
the NSAID includes diclofenac;
the calcium channel blocker includes verapamil;
the immunosuppressive component includes tacrolimus;
the anti-hypertensive includes minoxidil;
the hormone includes estriol;
the steroid includes finasteride;
the enzyme inhibitor includes tofacitinib; and
the solvent includes propylene glycol, water, alcohol, mineral oil, or combinations thereof.

* * * * *